(12) United States Patent
Chelliah et al.

(10) Patent No.: US 8,372,980 B2
(45) Date of Patent: Feb. 12, 2013

(54) FUSED RING THROMBIN RECEPTOR ANTAGONISTS

(75) Inventors: Mariappan V. Chelliah, Edison, NJ (US); Samuel Chackalamannil, Califon, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/188,520

(22) Filed: Jul. 22, 2011

(65) Prior Publication Data

US 2011/0301112 A1 Dec. 8, 2011

Related U.S. Application Data

(62) Division of application No. 11/734,057, filed on Apr. 11, 2007, now Pat. No. 8,003,803.

(60) Provisional application No. 60/791,748, filed on Apr. 13, 2006.

(51) Int. Cl.
| | |
|---|---|
| C07D 413/00 | (2006.01) |
| A01N 43/04 | (2006.01) |
| A01N 43/40 | (2006.01) |
| A01N 43/42 | (2006.01) |
| A61K 31/70 | (2006.01) |
| A61K 31/44 | (2006.01) |
| A61K 31/727 | (2006.01) |

(52) U.S. Cl. ......... 546/271.7; 514/48; 514/56; 514/338; 514/301

(58) Field of Classification Search .............. 514/48, 514/56, 338, 301; 546/271.7
See application file for complete search history.

(56) References Cited

U.S. PATENT DOCUMENTS

| | | | |
|---|---|---|---|
| 6,063,847 | A | 5/2000 | Chackalamannil et al. |
| 6,326,380 | B1 | 12/2001 | Chackalamannil et al. |
| 6,645,987 | B2 | 11/2003 | Chackalamannil et al. |
| 7,037,920 | B2 | 5/2006 | Chackalamannil et al. |
| 7,713,999 | B2 | 5/2010 | Chackalamannil et al. |
| 2003/0203927 | A1 | 10/2003 | Chackalamannil et al. |
| 2004/0152736 | A1 | 8/2004 | Chackalamannil et al. |

FOREIGN PATENT DOCUMENTS

| | | |
|---|---|---|
| WO | WO 94/03479 | 2/1994 |
| WO | WO 01/96330 | 12/2001 |

OTHER PUBLICATIONS

Bensaid et al., "The Cannabinoid CB1 Receptor Antagonist SR141716 Increases Acrp30 . . . ", Molecular Pharmacology, 63(4): 908-914 (2003).
Bernatowicz et al., "Development of Potent Thrombin Receptor Antagonist Peptides", J. Med. Chem., 39: 4879-4887 (1996).
Chackalamannil, "A Highly Efficient Total Synthesis of (+)-Himbacine", J. Am. Chem. Soc., 118: 9812-9813 (1996).
Pertwee, "Pharmacology of Cannabinoid Receptor Ligands", Current Medicinal Chemistry, 6(8): 635-664 (1999).
PCT International Search Report dated Jan. 2, 2008 for PCT Application No. PCT/US2007/008978.
Chackalamannil, et al., Journal of Medicinal Chemistry, (2005), pp. 5884-5887, vol. 48, No. 19.
Christine Espino & Du Bois, A Rh-Catalyzed C-H Insertion Reaction for the Oxidative Conversion of Carbamates to Oxazolidinones, 40 Angew. Chem. Intl Ed.598 (2001).

Primary Examiner — Sean Basquill
(74) Attorney, Agent, or Firm — Mark W. Russell

(57) ABSTRACT

Fused-ring, heterocyclic-substituted tricyclics of the formula

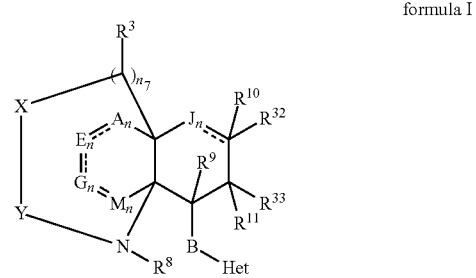

formula I or a pharmaceutically acceptable salt or solvate of said compound, isomer or racemic mixture wherein
----- represents an optional double bond, and wherein $A_n$, $E_n$, $M_n$, $G_n$, $J_n$, $R^3$, $n_7$, $R^8$, $R^9$, $R^{10}$, $R^{11}$, $R^{32}$, $R^{33}$, X, Y, B and Het are herein defined and the remaining substituents are as defined in the specification, are disclosed, as well as pharmaceutical compositions containing them and a method of treating diseases associated with thrombosis, atherosclerosis, restenosis, hypertension, angina pectoris, arrhythmia, heart failure, and cancer by administering said compounds. Combination therapy with other cardiovascular agents is also claimed.

11 Claims, No Drawings

FUSED RING THROMBIN RECEPTOR ANTAGONISTS

CROSS-REFERENCE TO RELATED APPLICATIONS

This application is a divisional application of application U.S. Ser. No. 11/734,057, which was filed Apr. 11, 2007 and is now allowed, which in turn claimed benefit of provisional application U.S. Ser. No. 60/791,748, filed on Apr. 13, 2006, all herein incorporated by reference.

BACKGROUND OF THE INVENTION

The present invention relates to himbacine derivatives, which can be useful as thrombin receptor antagonists in the treatment of diseases associated with thrombosis, atherosclerosis, restenosis, hypertension, angina pectoris, arrhythmia, heart failure, cerebral ischemia, stroke, neurodegenerative diseases and cancer. Thrombin receptor antagonists are also known as protease activated receptor-1 (PAR-1) antagonists. The compounds of the invention also can be useful as cannabinoid ($CB_2$) receptor inhibitors for the treatment of rheumatoid arthritis, systemic lupus erythematosus, multiple sclerosis, diabetes, osteoporosis, renal ischemia, cerebral stroke, cerebral ischemia, nephritis, inflammatory disorders of the lungs and gastrointestinal tract, and respiratory tract disorders such as reversible airway obstruction, chronic asthma and bronchitis. The invention also relates to pharmaceutical compositions comprising said compounds.

Thrombin is known to have a variety of activities in different cell types. Thrombin receptors are known to be present in such cell types as human platelets, vascular smooth muscle cells, endothelial cells and fibroblasts. It is therefore expected that thrombin receptor antagonists will be useful in the treatment of thrombotic, inflammatory, atherosclerotic and fibroproliferative disorders, as well as other disorders in which thrombin and its receptor play a pathological role.

Thrombin receptor antagonist peptides have been identified based on structure-activity studies involving substitutions of amino acids on thrombin receptors. In Bernatowicz et al., *J. Med. Chem.*, 39 (1996), p. 4879-4887, tetra- and pentapeptides are disclosed as being potent thrombin receptor antagonists, for example N-trans-cinnamoyl-p-fluoroPhe-p-guanidinoPhe-Leu-Arg-$NH_2$ and N-trans-cirinamoyl-p-fluoroPhe-p-guanidinoPhe-Leu-Arg-Arg-$NH_2$. Peptide thrombin receptor antagonists are also disclosed in WO 94/03479, published Feb. 17, 1994.

Cannabinoid receptors belong to the superfamily of G-protein coupled receptors. They are classified into the predominantly neuronal $CB_1$ receptors and the predominantly peripheral $CB_2$ receptors. These receptors exert their biological actions by modulating adenylate cyclase and $Ca^{+2}$ and $K^+$ currents. While the effects of $CB_1$ receptors are principally associated with the central nervous system, $CB_2$ receptors are believed to have peripheral effects related to bronchial constriction, immunomodulation and inflammation. As such, a selective $CB_2$ receptor binding agent is expected to have therapeutic utility in the control of diseases associated with rheumatoid arthritis, systemic lupus erythematosus, multiple sclerosis, diabetes, osteoporosis, renal ischemia, cerebral stroke, cerebral ischemia, nephritis, inflammatory disorders of the lungs and gastrointestinal tract, and respiratory tract disorders such as reversible airway obstruction, chronic asthma and bronchitis (R. G. Pertwee, *Curr. Med. Chem.* 6(8), (1999), 635; M. Bensaid, *Molecular Pharmacology*, 63 (4), (2003), 908.).

Himbacine, a piperidine alkaloid of the formula

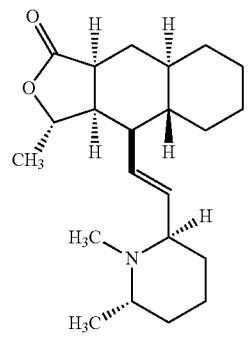

has been identified as a muscarinic receptor antagonist. The total synthesis of (+)-himbacine is disclosed in Chackalamannil et al., *J. Am. Chem. Soc.*, 118 (1996), p. 9812-9813.

Substituted tricyclic thrombin receptor antagonists are disclosed in U.S. Pat. No. 6,063,847, U.S. Pat. No. 6,326,380 and U.S. Ser. Nos. 09/880,222 (WO 01/96330) and 10/271,715.

SUMMARY OF THE INVENTION

The present invention relates to compounds represented by the formula I:

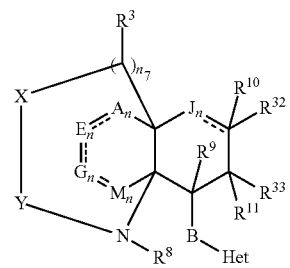

formula I or a pharmaceutically acceptable salt of said compound, wherein

===== represents a double bond or a single bond, as permitted by the valency requirement; with the proviso that $R^{10}$ is absent when the carbon to which $R^{10}$ is attached is part of a double bond;

B is —$(CH_2)_{n3}$—, —$(CH_2)$—O—, —$(CH_2)S$—, —$(CH_2)$—$NR^6$—, —$C(O)NR^6$—, —$NR^6C(O)$—,

—$(CH_2)_{n4}CR^{12}$=$CR^{12a}(CH_2)_{n5}$— or —$(CH_2)_{n4}C$≡C$(CH_2)_{n5}$—, wherein $n_3$ is 0-5, $n_4$ and $n_5$ are independently 0-2, and $R^{12}$ and $R^{12a}$ are independently selected from the group consisting of hydrogen, alkyl and halogen;

A, E, G, J and M are independently selected from the group consisting of —$N(R^{54})$—, —$(CR^1R^2)$—, —O—, —C(O)—, —S—, —S(O)— and —$S(O)_2$—; with the provisos that selection of A, E, G, J and M does not result in adjacent oxygen or sulfur atoms;

each n is 0, 1 or 2 with the provisos that the sum of the n variables is 1, 2 or 3;

X is —O—, —C(O)—, or —N($R^{15}$)—;

Y is —C(O)— or —SO$_2$—;

Het is a mono-, bi- or tricyclic heteroaromatic group of 5 to 14 atoms comprised of 1 to 13 carbon atoms and 1 to 4 heteroatoms independently selected from the group consisting of N, O and S, with the proviso that there are no adjacent oxygen or sulfur atoms present in the heteroaromatic group, wherein a ring nitrogen can form an N-oxide or a quaternary group with an alkyl group, wherein Het is attached to B by a carbon atom ring member, and wherein the Het group is substituted by 1 to 4 moieties, W, wherein each W is independently selected from the group consisting of hydrogen; alkyl; fluoroalkyl; difluoroalkyl; trifluoroalkyl; cycloalkyl; heterocycloalkyl; heterocycloalkyl substituted by alkyl or alkenyl; alkenyl; $R^{21}$-arylalkyl; $R^{21}$-aryl-alkenyl; heteroaryl; heteroarylalkyl; heteroarylalkenyl; hydroxyalkyl; dihydroxyalkyl; aminoalkyl; alkylaminoalkyl; di-(alkyl)-aminoalkyl; thioalkyl; alkoxy; alkenyloxy; halogen; —N$R^4R^5$; —CN; —OH; —C(O)O$R^{17}$; —CO$R^{16}$; —OS(O$_2$)CF$_3$; —CH$_2$OCH$_2$CF$_3$; alkylthio; —C(O)N$R^4R^5$; —OCHRE-phenyl; phenoxyalkyl; —NHCO$R^{16}$; —NHC(O)O$R^{16}$; —NHSO$_2R^{16}$; biphenyl; —OC($R^6$)$_2$COO$R^7$; —OC($R^6$)$_2$C(O)N$R^4R^5$; alkoxy substituted by alkyl, amino or —NHC(O)O$R^{17}$; $R^{21}$-aryl; $R^{21}$-heteroaryl; alkyl optionally substituted with —N$R^1R^2$, —N$R^1$CO$R^2$, —N$R^1$CON$R^1R^2$, —N$R^1$C(O)O$R^2$, —N$R^1$S(O)$_2R^2$, —N$R^1$S(O)$_2$N$R^1R^2$, —C(O)O$R^1$, —CON$R^1R^2$, heteroaryl, hydroxyalkyl or —S(O)$_2$-alkyl; or —C(O)N$R^4R^5$; wherein adjacent carbons on the Het ring can optionally form a ring with a methylenedioxy group;

$R^1$ and $R^2$ are independently selected from the group consisting of hydrogen, alkyl, fluoroalkyl, difluoroalkyl, trifluoroalkyl, cycloalkyl, alkenyl, alkoxy, arylalkyl, arylalkenyl, heteroarylalkyl, heteroarylalkenyl, hydroxy, hydroxyalkyl, alkoxyalkyl, aminoalkyl, aryl and thioalkyl; or $R^1$ and $R^2$ when attached to nitrogen, taken together, form a mono or bicyclic heterocyclic ring of 4 to 10 atoms, with 1-3 heteroatoms selected from —O—, —N—, —S—, —S(O)—, —S(O)$_2$— and —C(O)—, with the proviso that S and O ring atoms are not adjacent to each other, where said heterocyclic ring is unsubstituted or substituted with one or more groups selected from alkyl, halogen, hydroxy, alkoxy, aryloxy and arylalkoxy;

$R^3$ is H, optionally substituted alkyl, cycloalkyl, heterocycloalkyl, aryl or heteroaryl;

$n_7$ is 0 or 1;

$R^6$ is hydrogen, alkyl or phenyl;

$R^7$ is hydrogen or alkyl;

$R^8$ and $R^{15}$ are independently selected from the group consisting of hydrogen, alkyl, fluoroalkyl, difluoroalkyl, trifluoroalkyl, cycloalkyl, alkenyl, alkoxy, arylalkyl, arylalkenyl, heteroarylalkyl, heteroarylalkenyl, hydroxy, hydroxyalkyl, alkoxyalkyl, aminoalkyl, aryl and thioalkyl each $R^{13}$ is independently selected from hydrogen, alkyl, cycloalkyl, haloalkyl, halogen, —(CH$_2$)$_{n6}$NHC(O)O$R^{16b}$, —(CH$_2$)$_{n6}$NHC(O)$R^{16b}$, —(CH$_2$)$_{n6}$NHC(O)N$R^4R^5$, —(CH$_2$)$_{n6}$NHSO$_2R^{16}$, —(CH$_2$)$_{n6}$NHSO$_2$N$R^4R^5$, and —(CH$_2$)$_{n6}$C(O)N$R^{28}R^{29}$, where $n_6$ is 0-4;

each $R^{14}$ is independently selected from the group consisting of hydrogen, alkyl, —OH, alkoxy, arylalkyl, heteroaryl, heteroarylalkyl, heterocyclyl, heterocyclylalkyl, halogen, haloalkyl, —(CH$_2$)$_{n6}$NHC(O)O$R^{16b}$, —(CH$_2$)$_{n6}$NHC(O)$R^{16b}$, —(CH$_2$)$_{n6}$NHC(O)N$R^4R^5$, —(CH$_2$)$_{n6}$NHSO$_2R^{16}$, —(CH$_2$)$_{n6}$NHSO$_2$N$R^4R^5$, and —(CH$_2$)$_{n6}$C(O)N$R^{28}R^{29}$ where $n_6$ is 0-4; where $R^4$ and $R^5$ are independently selected from the group consisting of hydrogen, alkyl, phenyl, benzyl and cycloalkyl, or $R^4$ and $R^5$ together can form a ring with the nitrogen to which they are attached, wherein said ring formed by $R^4$ and $R^5$ is optionally substituted with =O, OH, O$R^1$ or —C(O)OH; or $R^{13}$ and $R^{14}$ taken together form a spirocyclic or a heterospirocyclic ring of 3-6 ring atoms, wherein said heterospirocyclic ring contains 2 to 5 carbon ring atoms and 1 or 2 hetero ring atoms selected from the group consisting of O, S and N;

$R^{16}$ is independently selected from the group consisting of hydrogen, alkyl, phenyl and benzyl;

$R^{16a}$ is independently selected from the group consisting of hydrogen, alkyl, phenyl and benzyl;

$R^{16b}$ is hydrogen, alkoxy, alkyl, alkoxyalkyl-, $R^{22}$—O—C(O)-alkyl-, cycloalkyl, $R^{21}$-aryl, $R^{21}$-arylalkyl, haloalkyl, alkenyl, halo substituted alkenyl, alkynyl, halo substituted alkynyl, $R^{21}$-heteroaryl, ($R^{21}$-heteroaryl)-alkyl-, ($R^{21}$-heterocycloalkyl)-alkyl-, $R^{28}R^{29}$N-alkyl-, $R^{28}R^{29}$N—C(O)-alkyl-, $R^{28}R^{29}$N—C(O)O-alkyl-, $R^{28}$OC(O)N($R^{29}$)-alkyl-, $R^{28}$S(O)$_2$N($R^{29}$)-alkyl-, $R^{28}R^{29}$N—C(O)—N($R^{29}$)-alkyl-, $R^{28}R^{29}$N—S(O)$_2$N($R^{29}$)-alkyl-, $R^{28}$—C(O)N($R^{29}$)-alkyl-, $R^{28}R^{29}$N—S(O)$_2$-alkyl-, HOS(O)$_2$-alkyl-, (OH)$_2$P(O)$_2$-alkyl-, $R^{28}$—S-alkyl-, $R^{28}$—S(O)$_2$-alkyl- or hydroxyalkyl;

$R^{17}$ is independently selected from the group consisting of hydrogen, alkyl, phenyl and benzyl;

$R^{18}$ and $R^{19}$ are hydrogen, alkyl, aryl, $R^{21}$-aryl, heteroaryl, cycloalkyl, heterocyclyl, alkoxyalkyl, haloalkoxyalkyl, aryloxyalkyl, arylalkoxyalkyl, heteroaryloxyalkyl, heteroarylalkoxyalkyl, cycloalkyloxyalkyl, (heterocyclyl)alkyloxyalkyl, alkoxyalkyloxyalkyl, —S(O)$_2$-alkyl, —C(NH)N$R^1R^2$ or alkyl substituted with one or two moieties selected from cycloalkyl, halogen, hydroxy, —N$R^1$, $R^2$, —N$R^1$C(O)$R^2$, —N$R^1$C(O)N$R^1$, $R^2$, —N$R^1$C(O)O$R^2$, —N$R^1$S(O)$_2R^2$, —N$R^1$S(O)$_2$N$R^1R^2$, —C(O)OH, —C(O)O$R^1$ and —C(O)N$R^1R^2$; or $R^{18}$ and $R^{19}$ together with the nitrogen to which they are attached, form a mono or bicyclic heterocyclic ring of 4 to 10 atoms, having 1-3 hetero ring atoms selected from —O—, —N—, —S—, —S(O)$_2$— and —C(O)—, with the proviso that S and O atoms are not adjacent to each other, the ring being unsubstituted or substituted with one or more groups selected from alkyl, halogen, hydroxy, alkoxy, aryloxy, arylalkoxy, —N$R^1R^2$, —N$R^1$CO$R^2$, —N$R^1$C(O)N$R^1R^2$, —N$R^1$C(O)O$R^2$, —N$R^1$S(O)$_2R^2$, —N$R^1$S(O)$_2$N$R^1R^2$, —C(O)O$R^1$, —CON$R^1R^2$ and alkyl substituted with —N$R^1R^2$, —N$R^1$CO$R^2$, —N$R^1$CON$R^1R^2$, —N$R^1$C(O)O$R^2$, —N$R^1$S(O)$_2R^2$, —N$R^1$S(O)$_2$N$R^1R^2$, —C(O)O$R^1$ or —CON$R^1R^2$;

$R^{21}$ is 1 to 3 moieties and each $R^{21}$ is independently selected from the group consisting of hydrogen, —CN, —CF$_3$, —OCF$_3$, halogen, —NO$_2$, alkyl, —OH, alkoxy, alkylamino-, di-(alkyl)amino-, —N$R^{25}R^{26}$alkyl-, hydroxyalkyl-, —C(O)O$R^{17}$, —CO$R^{17}$, —NHCO$R^{16}$, —NHS(O)$_2R^{16}$, —C(NH)—NH$_2$, —NHS(O)$_2$CH$_2$CF$_3$, —C(O)N$R^{25}R^{26}$, —N$R^{25}$—C(O)—N$R^{25}R^{26}$, —S(O)$R^{16}$, —S(O)$_2R^{16}$, —S$R^{16}$; —SO$_2$N$R^4R^5$ and —CON$R^4$, $R^5$; or two adjacent $R^{21}$ moieties can form a methylenedioxy group;

$R^{22}$ is hydrogen, alkyl, phenyl, benzyl, —CO$R^{16}$, —CON$R^{18}R^{19}$, —CO$R^{23}$, —S(O)$R^{31}$, —S(O)$_2R^{31}$, —S(O)$_2$N$R^{24}R^{25}$ or —C(O)O$R^{27}$;

$R^{23}$ is

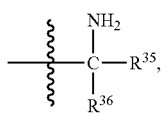

wherein $R^{35}$ and $R^{36}$ are independently selected from the group consisting of hydrogen, alkyl, and $R^{37}$-substituted alkyl, wherein $R^{37}$ is selected from the group consisting of HO—, HS—, $CH_2S$—, —$NH_2$, phenyl, p-hydroxyphenyl and indolyl; or $R^{23}$ is alkyl; haloalkyl; alkenyl; haloalkenyl; alkynyl; cycloalkyl; cycloalkylalkyl; cycloalkyl substituted by 1 to 3 substituents selected from the group consisting of alkoxyalkyl, alkyl, halogen, hydroxy, alkoxy, aryloxy, arylalkoxy, —$NR^1R^2$, —$NR^1C(O)R^2$, —$NR^1C(O)NR^1R^2$, —$NR^1C(O)OR^2$, —$NR^1S(O)_2R^2$, —$NR^1S(O)_2NR^1R^2$, —$C(O)OR^1$ and —$CONR^1R^2$; aryl; aralkyl; heteroaryl; heterocycloalkyl; alkyl substituted with —$NR^1R^2$, —$NR^1COR^2$, —$NR^1CONR^1R^2$, —$NR^1C(O)OR^2$, —$NR^1S(O_2)R^2$, —$NR^1S(O_2)NR^1R^2$, —$C(O)OR^1$, —$CONR^1R^2$ and —$SO_3H$;

$R^{24}$, $R^{25}$ and $R^{26}$ are independently selected from the group consisting of hydrogen, alkyl, haloalkyl, alkenyl, alkynyl, aryl, aralkyl, cycloalkyl, halocycloalkyl, alkoxyalkyl, hydroxy and alkoxy;

$R^{27}$ is 1 to 3 moieties and each $R^{27}$ is selected from the group consisting of hydrogen, alkyl, and cycloalkyl, wherein $R^{27}$ is optionally substituted with —OH, —C(O)OH, halogen and alkoxy;

$R^{28}$ and $R^{29}$ are independently selected from the group consisting of hydrogen, alkyl, alkoxy, arylalkyl, heteroaryl, heteroarylalkyl, hydroxyalkyl, alkoxyalkyl, heterocyclyl, heterocyclylalkyl, and haloalkyl; or $R^{28}$ and $R^{29}$ taken together form a spirocyclic or a heterospirocyclic ring having 3-6 ring atoms;

$R^{32}$ and $R^{33}$ are independently selected from the group consisting of hydrogen, $R^{34}$-alkyl, $R^{34}$-alkenyl, $R^{34}$-alkynyl, e-heterocycloalkyl, $R^{38}$-aryl, $R^{38}$-aralkyl, $R^{42}$-cycloalkyl, $R^{42}$-cycloalkenyl, —OH, —$OC(O)R^{43}$, —$C(O)OR^{43}$, —$C(O)R^{43}$, —$C(O)NR^{43}R^{44}$, —$NR^{43}R^{44}$, —$NR^{43}C(O)R^{44}$, —$NR^{43}C(O)OR^{44}$, —$NR^{43}C(O)NR^{44}R^{45}$, —$NHS(O)_2R^{43}$, —$OC(O)NR^{43}R^{44}$, $R^{37}$-alkoxy, $R^{37}$-alkenyloxy, $R^{37}$-alkynyloxy $R^{40}$-heterocycloalkyloxy, $R^{42}$-cycloalkyloxy, $R^{42}$-cyclo-alkenyloxy, $R^{42}$-cycloalkyl-NH—, —$NHSO_2NHR^{16}$ and —CH(=$NOR^{17}$);

or $R^{32}$ and $R^{33}$ are combined to form a ring structure Q, below

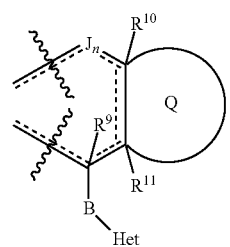

where
$R^9$ is hydrogen, OH, alkoxy, halogen or haloalkyl;
Q is fused R-substituted aryl, R-substituted heteroaryl, R-substituted heterocyclic ring of 4-8 atoms containing 1-3 heteroatoms selected from O, S, S(O), $S(O)_2$ and $NR^{22}$ with the proviso that S and O cannot be adjacent to one another; or Q is

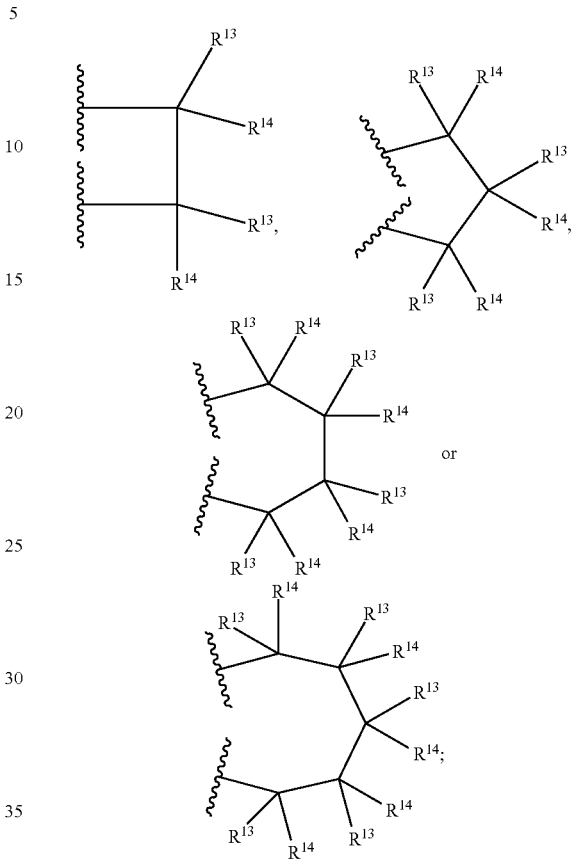

wherein $R^{10}$ and $R^{11}$ are independently selected from the group consisting of $R^1$, fluoroalkoxy, difluoroalkoxy, trifluoroalkoxy, cycloalkyloxy, alkenyloxy, arylalkoxy, arylalkenyloxy, heteroarylalkoxy, heteroarylalkenyloxy, hydroxyalkoxy, alkoxyalkoxy, aminoalkoxy, aryloxy and thioalkoxy, provided that when ring Q is aromatic and the carbon atoms bearing $R^{10}$ and $R^{11}$ are connected by a double bond, $R^{10}$ and $R^{11}$ are absent;

R is 1 to 5 moieties and each R is independently selected from the group consisting of hydrogen, alkyl, halogen, hydroxy, amino, alkylamino, dialkylamino, alkoxy, —$COR^{16}$, —$C(O)OR^{17}$, —$C(O)NR^4R^5$, —$SOR^{16}$, —$S(O_2)R^{16}$, —$NR^{16}COR^{16a}$, —$NR^{16}C(O)OR^{16a}$, —$NR^{16}CONR^4R^5$, —$NR^{16}S(O_2)NR^4R^5$, fluoroalkyl, difluoroalkyl, trifluoroalkyl, cycloalkyl, alkenyl, arylalkyl, arylalkenyl, heteroarylalkyl, heteroarylalkenyl, hydroxyalkyl, aminoalkyl, aryl and thioalkyl;

$R^{34}$ is 1 to 3 moieties and each $R^{34}$ is independently selected from the group consisting of hydrogen, halogen, —OH, alkoxy, $R^{47}$-aryl, alkyl-C(O)—, alkenyl-C(O)—, alkynyl-C(O)—, heterocycloalkyl, $R^{39}$-cycloalkyl, $R^{39}$-cycloalkenyl, —$OC(O)R^{43}$, —$C(O)OR^{43}$, —$C(O)R^{43}$, —$C(O)NR^{43}R^{44}$, —$NR^{43}R^{44}$, —$NR^{43}C(O)R^{44}$, —$NR^{43}C(O)NR^{44}R^{45}$, —$NHSO_2R^{43}$, —$OC(O)NR^{43}R^{44}$, $R^{39}$-alkenyloxy, $R^{39}$-alkynyloxy, $R^{40}$-heterocycloalkyloxy, $R^{42}$-cycloalkyloxy, $R^{42}$-cycloalkenyloxy, $R^{42}$-cycloalkyl-NH—, —$NHSO_2NHR^{16}$ and —CH(=$NOR^{17}$);

$R^{38}$ is 1 to 3 moieties and each $R^{38}$ is independently selected from the group consisting of hydrogen, heterocycloalkyl, halogen, —C(O)OR$^{48}$, —CN, —C(O)NR$^{49}$R$^{50}$, —NR$^{51}$C(O)R$^{52}$, —OR$^{48}$, cycloalkyl, cycloalkylalkyl, alkylcycloalkylalkyl, haloalkylcycloalkylalkyl, hydroxyalkyl, alkoxyalkyl, and R$^{52}$-heteroaryl; or two R$^{38}$ groups on adjacent ring carbons form a fused methylenedioxy group;

R$^{39}$ is 1 to 3 moieties and each R$^{39}$ is independently selected from the group consisting of hydrogen, halogen and alkoxy;

R$^{40}$ is 1 to 3 moieties and each R$^{40}$ is independently selected from the group consisting of hydrogen, R$^{41}$-alkyl, R$^{41}$-alkenyl and R$^{41}$-alkynyl;

R$^{41}$ is hydrogen, —OH or alkoxy;

R$^{42}$ is 1 to 3 moieties and each R$^{42}$ is independently selected from the group consisting of hydrogen, alkyl, —OH, alkoxy and halogen;

R$^{43}$, R$^{44}$ and R$^{45}$ are independently selected from the group consisting of hydrogen, alkyl, alkoxyalkyl, R$^{38}$-arylalkyl, R$^{48}$-cycloalkyl, R$^{53}$-cycloalkylalkyl, R$^{38}$-aryl, heterocycloalkyl, heteroaryl, heterocycloalkylalkyl and heteroarylalkyl;

R$^{46}$ is hydrogen, alkyl, hydroxyalkyl or alkoxy;

R$^{47}$ is 1 to 3 moieties and each R$^{47}$ is independently selected from the group consisting of hydrogen, alkyl, —OH, halogen, —CN, alkoxy, trihaloalkoxy, alkylamino, di(alkyl)amino, —OCF$_3$, hydroxyalkyl, —CHO, —C(O)alkylamino, —C(O)di(alkyl)amino, —NH$_2$, —NHC(O)alkyl and —N(alkyl)C(O)alkyl;

R$^{48}$ is hydrogen, alkyl, haloalkyl, dihaloalkyl or trifluoroalkyl;

R$^{49}$ and R$^{50}$ are independently selected from the group consisting of hydrogen, alkyl, aralkyl, phenyl and cycloalkyl, or R$^{49}$ and R$^{50}$ together are —(CH$_2$)$_4$—, —(CH$_2$)$_5$— or —(CH$_2$)$_2$—NR$^{39}$—(CH$_2$)$_2$— and form a ring with the nitrogen to which they are attached;

R$^{51}$ and R$^{52}$ are independently selected from the group consisting of hydrogen, alkyl, aralkyl, phenyl and cycloalkyl, or R$^{51}$ and R$^{52}$ in the group —NR$^{39}$C(O)R$^{40}$, together with the nitrogen atoms to which they are attached, form a cyclic lactam having 5-8 ring members;

R$^{53}$ is hydrogen, alkoxy, —SOR$^{16}$, —SO$_2$R$^{17}$, —C(O)OR$^{17}$, —C(O)NR$^{18}$R$^{19}$, alkyl, halogen, fluoroalkyl, difluoroalkyl, trifluoroalkyl, cycloalkyl, alkenyl, aralkyl, arylalkenyl, heteroarylalkyl, heteroarylalkenyl, hydroxyalkyl, aminoalkyl, aryl, thioalkyl, alkoxyalkyl or alkylaminoalkyl; and R$^{54}$ is selected from the group consisting of hydrogen; alkyl; fluoroalkyl; difluoroalkyl; trifluoroalkyl; cycloalkyl; cycloalkyl substituted by 1 to 3 substituents selected from the group consisting of alkoxyalkyl, alkyl, halogen, hydroxy, alkoxy, aryloxy, arylalkoxy, —NR$^1$R$^2$, —NR$^1$C(O)R$^2$, —NR$^1$C(O)NR$^1$R$^2$, —NR$^1$C(O)OR$^2$, —NR$^1$S(O)$_2$R$^2$, —NR$^1$S(O)$_2$NR$^1$R$^2$, —C(O)OH, —C(O)OR$^1$ and —CONR$^1$R$^2$; alkenyl; alkoxy; arylalkyl; arylalkenyl; heteroarylalkyl; heteroarylalkenyl; hydroxy; alkoxy; hydroxyalkyl; alkoxyalkyl; aminoalkyl; aryl; heteroaryl; thioalkyl and alkyl substituted by 1 to 3 substituents selected from the group consisting of urea, sulfonamide, carboxamide, carboxylic acid, carboxylic ester and sulfonyl urea.

Pharmaceutical compositions comprising at least one compound of formula I and a pharmaceutically acceptable carrier are also provided.

The compounds of the present invention can be useful as Thrombin receptor antagonists, also known as PAR-1 antagonists, or as cannabinoid (CB$_2$) receptor antagonists. Thrombin receptor antagonist compounds of the present invention can have anti-thrombotic, anti-platelet aggregation, anti-atherosclerotic, anti-restenotic anti-coagulant, and/or anti-inflammatory activity. CB$_2$ receptor inhibitor compounds of the present invention can be useful for the treatment of rheumatoid arthritis, systemic lupus erythematosus, multiple sclerosis, diabetes, osteoporosis, renal ischemia, cerebral stroke, cerebral ischemia, nephritis, inflammatory disorders of the lungs and gastrointestinal tract, and respiratory tract disorders such as reversible airway obstruction, chronic asthma and bronchitis.

Compounds of the invention can be useful for the treatment of thrombosis, atherosclerosis, restenosis, hypertension, angina pectoris, angiogenesis related disorders, arrhythmia, a cardiovascular or circulatory disease or condition, heart failure, acute coronary syndrome (ACS), myocardial infarction, glomerulonephritis, thrombotic stroke, thromboembolytic stroke, peripheral vascular diseases, deep vein thrombosis, venous thromboembolism, a cardiovascular disease associated with hormone replacement therapy, disseminated intravascular coagulation syndrome, cerebral infarction, migraine, erectile dysfunction, rheumatoid arthritis, rheumatism, astrogliosis, a fibrotic disorder of the liver, kidney, lung or intestinal tract, systemic lupus erythematosus, multiple sclerosis, osteoporosis, renal disease, acute renal failure, chronic renal failure, renal vascular homeostasis, renal ischemia, bladder inflammation, diabetes, diabetic neuropathy, cerebral stroke, cerebral ischemia, nephritis, cancer, melanoma, renal cell carcinoma, neuropathy, malignant tumors, neurodegenerative and/or neurotoxic diseases, conditions or injuries, Alzheimer's disease, an inflammatory disease or condition, asthma, glaucoma, macular degeneration, psoriasis, endothelial dysfunction disorders of the liver, kidney or lung, inflammatory disorders of the lungs and gastrointestinal tract, respiratory tract disease or condition, radiation fibrosis, endothelial dysfunction, periodontal diseases or wounds, or a spinal cord injury, or a symptom or result thereof, as well as other disorders in which thrombin and its receptor play a pathological role.

In particular, compounds of the present invention are used to treat acute coronary syndrome, myocardial infarction of thrombotic stroke.

Compounds of the present invention can also be used in a method to treat or prevent a condition associated with cardiopulmonary bypass surgery (CPB) comprising administering an effective amount of at least one thrombin receptor antagonist to a subject of said surgery. CPB surgery includes coronary artery bypass surgery (CABG), cardiac valvular repair and replacement surgery, pericardial and aortic repair surgeries. In particular, the present invention relates to a method of treating or preventing a condition associated with CABG surgery comprising administering an effective amount of at least one thrombin receptor antagonist to a subject of said surgery. The conditions associated with CABG are selected from the group consisting of: bleeding; thrombotic vascular events such as thrombosis, restenosis; vein graft failure; artery graft failure; atherosclerosis, angina pectoris; myocardial ischemia; acute coronary syndrome myocardial infarction; heart failure; arrhythmia; hypertension; transient ischemic attack; cerebral function impairment; thromboembolic stroke; cerebral ischemia; cerebral infarction; thrombophlebitis; deep vein thrombosis; and, peripheral vascular disease.

In another embodiment, compounds of the present invention are useful in a method for treating and/or preventing radiation- and/or chemical-induced toxicity in non-malignant tissue in a patient comprising administering a therapeutically effective amount of a compound of formula I. In particular, the radiation- and/or chemical-induced toxicity is one or more of intestinal fibrosis, pneumonitis, and mucositis. In a preferred embodiment, the radiation- and/or chemical-induced toxicity is intestinal fibrosis. In another preferred embodiment, the radiation- and/or chemical-induced toxicity is oral mucositis. In yet another embodiment, the radiation- and/or chemical-induced toxicity is intestinal mucositis, intestinal fibrosis, intestinal radiation syndrome, or pathophysiological manifestations of intestinal radiation exposure.

The present invention also provides methods for reducing structural radiation injury in a patient that will be exposed, is concurrently exposed, or was exposed to radiation and/or chemical toxicity, comprising administering a therapeutically effective amount of a compound of formula I. The present invention also provides methods for reducing inflammation in a patient that will be exposed, is concurrently exposed, or was exposed to radiation and/or chemical toxicity, comprising administering a therapeutically effective amount of a compound of formula I. The present invention also provides methods for adverse tissue remodeling in a patient that will be exposed, is concurrently exposed, or was exposed to radiation and/or chemical toxicity, comprising administering a therapeutically effective amount of a compound of formula I. The present invention also provides methods for reducing fibroproliferative tissue effects in a patient that will be exposed, is concurrently exposed, or was exposed to radiation and/or chemical toxicity, comprising administering a therapeutically effective amount of a compound of formula I.

The present invention further provides methods useful for treating a cell proliferative disorder in a patient suffering therefrom comprising administering a therapeutically effective amount of a compound of formula I. In one embodiment, the cell proliferative disorder is pancreatic cancer, glioma, ovarian cancer, colorectal and/or colon cancer, breast cancer, prostate cancer, thyroid cancer, lung cancer, melanoma, or stomach cancer. In one embodiment, the glioma is an anaplastic astrocytoma. In another embodiment, the glioma is a glioblastoma multiforme.

As used above, the term inflammatory disease or condition includes irritable bowel syndrome, Crohn's disease, nephritis or a radiation- or chemotherapy-induced proliferative or inflammatory disorder of the gastrointestinal tract, lung, urinary bladder, gastrointestinal tract or other organ. The term respiratory tract disease or condition includes reversible airway obstruction, asthma, chronic asthma, bronchitis or chronic airways disease. "Cancer" includes renal cell carcinoma or an angiogenesis related disorder. "Neurodegenerative disease" includes Parkinson's disease, amyotropic lateral sclerosis, Alzheimer's disease, Huntington's disease or Wilson's disease.

Certain embodiments of this invention also relate to a method of using an effective amount of at least one compound of Formula I in combination with one or more additional agents for the treatment of thrombosis, atherosclerosis, restenosis, hypertension, angina pectoris, angiogenesis related disorders, arrhythmia, a cardiovascular or circulatory disease or condition, heart failure, acute coronary syndrome (ACS), myocardial infarction, glomerulonephritis, thrombotic stroke, thromboembolytic stroke, peripheral vascular diseases, deep vein thrombosis, venous thromboembolism, a cardiovascular disease associated with hormone replacement therapy, disseminated intravascular coagulation syndrome, cerebral infarction, migraine, erectile dysfunction, rheumatoid arthritis, rheumatism, astrogliosis, a fibrotic disorder of the liver, kidney, lung or intestinal tract, systemic lupus erythematosus, multiple sclerosis, osteoporosis, renal disease, acute renal failure, chronic renal failure, renal vascular homeostasis, renal ischemia, bladder inflammation, diabetes, diabetic neuropathy, cerebral stroke, cerebral ischemia, nephritis, cancer, melanoma, renal cell carcinoma, neuropathy, malignant tumors, neurodegenerative and/or neurotoxic diseases, conditions or injuries, Alzheimer's disease, an inflammatory disease or condition, asthma, glaucoma, macular degeneration, psoriasis, endothelial dysfunction disorders of the liver, kidney or lung, inflammatory disorders of the lungs and gastrointestinal tract, respiratory tract disease or condition, radiation fibrosis, endothelial dysfunction, periodontal diseases or wounds, or a spinal cord injury, or a symptom or result thereof. It is contemplated that a combination of this invention may be useful in treating more than one of the diseases listed.

For treating and/or preventing radiation- and/or chemical-induced toxicity in non-malignant tissue, the present invention includes administering to a patient in need of such treatment an effective amount of a combination of one or more compounds of formula I and one or more radiation-response modifiers selected from the group consisting of Kepivance™ (palifermin), L-glutamine, teduglutide, sucralfate mouth rinses, iseganan, lactoferrin, mesna and trefoil factor.

For treating a cell proliferative disorder the present invention includes administering to a patient in need of such treatment an effective amount of a combination of one or more compounds of formula I and another antineoplastic agent. In one embodiment, the other antineoplastic agent is temozolomide and the cell proliferative disorder is glioma. In another embodiment, the other antineoplastic agent is interferon and the cell proliferative disorder is melanoma. In one embodiment, the other antineoplastic agent is PEG-Intron (peginterferon alpha-2b) and the cell proliferative disorder is melanoma.

Pharmaceutical compositions comprising a therapeutically effective amount of a combination of at least one compound of formula I and at least one additional cardiovascular agent in a pharmaceutically acceptable carrier are also provided.

Pharmaceutical compositions comprising a therapeutically effective amount of a combination of at least one compound of formula I and a radiation-response modifier in a pharmaceutically acceptable carrier are also provided.

Pharmaceutical compositions comprising a therapeutically effective amount of a combination of at least one compound of formula I and an antineoplastic agent in a pharmaceutically acceptable carrier are also provided.

It is further contemplated that the combination of the invention can be provided as a kit comprising in a single package at least one compound of formula I in a pharmaceutical composition, and at least one separate pharmaceutical composition comprising a cardiovascular agent, a radiation-response modifier, or an antineoplastic agent.

DETAILED DESCRIPTION

In one embodiment, the present invention provides compounds represented by structural formula I, or pharmaceutically acceptable salt thereof, wherein the various moieties are as described as above.

For compounds of Formula I, preferred embodiments of the compounds of formula I are as follows:

An embodiment of a compound of formula I, wherein $A_n$ is —C(O)—.

An embodiment of a compound of formula I wherein $E_n$ is —O—.

An embodiment of a compound of formula I, wherein $G_n$ is —C(R$^1$R$^2$)—.

An embodiment of a compound of formula I, wherein $G_n$ is —C(R$^1$R$^2$)—, R$^1$ is H and R$^2$ is alkyl, preferably methyl.

An embodiment of a compound of formula I, wherein "n" in $M_n$ is 0.

An embodiment of a compound of formula I wherein $n_7$ is 0.

An embodiment of a compound of formula I wherein X is —O—.

An embodiment of a compound of formula I wherein Y is —C(O)—.

An embodiment of a compound of formula I wherein $R^8$ is H.

An embodiment of a compound of formula I, wherein $R^{32}$ and $R^{33}$ are combined to form the ring structure Q.

Another embodiment of a compound of formula I, wherein Q is

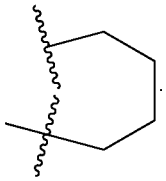 [SMILES: *CCCC*]

An embodiment of a compound of formula I, wherein $R^{32}$ is alkyl, preferably methyl, $R^{33}$ is alkyl, preferably methyl, $R^{19}$ is H, and $R^{11}$ is H.

Another embodiment of a compound of formula I, wherein $A_n$ is —C(O)—; $G_n$ is —C($R^1R^2$)—; E is —O—; the "n" in $M_n$ is 0; and $R^{32}$ and $R^{33}$ are combined to form a ring structure Q.

Another embodiment of a compound of formula I, wherein $A_n$ is —C(O)—; $G_n$ is —C($R^1R^2$)—; E is —O—; the "n" in $M_n$ is 0; and wherein $R^{32}$ is alkyl, preferably methyl, $R^{33}$ is alkyl, preferably methyl, $R^{19}$ is H, and $R^{11}$ is H.

Another embodiment of a compound of formula I, wherein B is —$(CH_2)_{n4}CR^{12}$=$CR^{12a}(CH_2)_{n5}$— wherein $n_4$ and $n_5$ are 0.

Another embodiment of a compound of formula I wherein Het is W-substituted pyridyl.

Another embodiment of a compound of formula I, wherein W is aryl, heteroaryl or aryl substituted by halogen or —CN.

An additional embodiment of a compound of formula I, wherein $J_n$ is —$CH_2$— where n is 1.

An additional embodiment of a compound of formula I, wherein $R^9$ is H.

An additional embodiment of a compound of formula I, wherein $A_n$ is —C(O)—; $G_n$ is —C($R^1R^2$)—; E is —O—; the "n" in $M_n$ is 0; $n_7$ is 0; X is —O—; Y is —C(O)—; $R^8$ is H; $R^{32}$ is alkyl, preferably methyl, $R^{33}$ is alkyl, preferably methyl, $R^{19}$ is H, and $R^{11}$ is H; or $R^{32}$ and $R^{33}$ together form the ring Q, wherein Q is

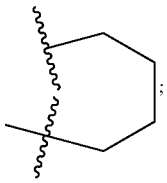 [SMILES: *CCCC*]

Het is W-substituted pyridyl; B is —$(CH_2)_{n4}CR^{12}$=$CR^{12a}$ $(CH_2)_{n5}$— wherein $n_4$ and $n_5$ are 0; $J_n$ is —$CH_2$— where n is 1; and $R^9$ is H.

As used above, and throughout this disclosure, the following terms, unless otherwise indicated, shall be understood to have the following meanings:

"Patient" includes both human and animals.

"Subject" includes both mammals and non-mammalian animals.

"Mammal" means humans and other mammalian animals.

The following definitions apply regardless of whether a term is used by itself or in combination with other terms, unless otherwise indicated. Therefore, the definition of "alkyl" applies to "alkyl" as well as the "alkyl" portions of "hydroxyalkyl", "haloalkyl", "alkoxy", etc.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Alkenyl" means an aliphatic hydrocarbon group (straight or branched carbon chain) comprising one or more double bonds in the chain and which can be conjugated or unconjugated. Useful alkenyl groups can comprise 2 to about 15 carbon atoms in the chain, preferably 2 to about 12 carbon atoms in the chain, and more preferably 2 to about 6 carbon atoms in the chain. The alkenyl group can be substituted by one or more substituents independently selected from the group consisting of halo, alkyl, aryl, cycloalkyl, cyano and alkoxy. Non-limiting examples of suitable alkenyl groups include ethenyl, propenyl, n-butenyl, 3-methylbut-enyl and n-pentenyl.

Where an alkyl or alkenyl chain joins two other variables and is therefore bivalent, the terms alkylene and alkenylene, respectively, are used.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl, 3-methylbutynyl, n-pentynyl, and decynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl, naphthyl, indenyl, tetrahydronaphthyl and indanyl. "Arylene" means a bivalent phenyl group, including ortho, meta and para-substitution.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

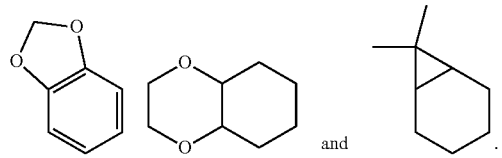

The term "Boc" refers to N-tert-butoxycarbonyl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclobutyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl.

"Cycloalkylene" refers to a corresponding bivalent ring, wherein the points of attachment to other groups include all positional isomers.

"Dihydroxyalkyl" refers to an alkyl chain substituted by two hydroxy groups on two different carbon atoms.

"Fluoroalkyl", "difluoroalkyl" and "trifluoroalkyl" mean alkyl chains wherein the terminal carbon is substituted by 1, 2 or 3 fluoroatoms, respectively, e.g., —CF$_3$, —CH$_2$CF$_3$, —CH$_2$CHF$_2$ or —CH$_2$CH$_2$F.

"Halo" refers to fluorine, chlorine, bromine or iodine radicals. Preferred are fluoro, chloro or bromo, and more preferred are fluoro and chloro.

"Halogen" means fluorine, chlorine, bromine, or iodine. Preferred are fluorine, chlorine and bromine.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination, provided that the rings do not include adjacent oxygen and/or sulfur atoms. N-oxides of the ring nitrogens are also included, as well as compounds wherein a ring nitrogen is substituted by an alkyl group to form a quaternary amine. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, oxadiazolyl, tetrazolyl, pyrimidyl, furazanyl, pyrrolyl, pyrazolyl, triazolyl, 1,2,4-thiadiazolyl, pyrazinyl, pyridazinyl, quinoxalinyl, phthalazinyl, oxindolyl, naphthyridyl (e.g., 1,5 or 1,7), pyrido[2,3]imidazolyl, imidazo[1,2-a]pyridinyl, imidazo[2,1-b]thiazolyl, benzofuranyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzoxazolyl, benzothiazolyl, pyridopyrimidinyl, 7-azaindolyl and the like. The term "heteroaryl" also refers to partially saturated heteroaryl moieties such as, for example, tetrahydrolsoquinolyl, tetrahydroquinolyl and the like. All positional isomers are contemplated, e.g., 2-pyridyl, 3-pyridyl and 4-pyridyl.

The term "Het" is exemplified by the single ring, bicyclic and benzofused heteroaryl groups as defined immediately above. Het groups are joined to group B by a carbon ring member, e.g., Het is 2-pyridyl, 3-pyridyl or 2-quinolyl. The Het ring can be substituted on any available ring carbon by a group W; 1 to 4 W substituents can be present on a Het ring.

"Heterocyclyl" or "heterocycloalkyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxanyl, 1,4-dioxanyl, tetrahydrofuranyl, tetrahydrothiopyranyl, tetrahydrothiophenyl, lactam, lactone, and the like.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

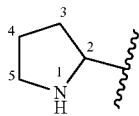

there is no —OH attached directly to carbons marked 2 and 5.

It should also be noted that tautomeric forms such as, for example, the moieties:

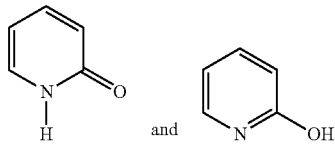 [SMILES: O=c1cccc[nH]1 ; Oc1ccccn1]

are considered equivalent in certain embodiments of this invention.

The term "heterospirocyclic" refers to a spirocyclic structure containing 3 to 5 carbon atoms and 1 or 2 heteroatoms selected from the group consisting of N, S and O, provided that the heteroatoms are not adjacent.

"Alkylamino" means an alkyl-amino group in which the alkyl group is as previously described. The bond to the parent moiety is through the amino.

"Alkylaminoalkyl" means an alkyl-amino-alkyl group in which the alkyl groups are as previously described. The bond to the parent moiety is through the alkyl.

"Alkylcycloalkylalkyl" means an alkyl-cycloalkyl-alkyl group in which the alkyl and cycloalkyl groups are as previously described. The bond to the parent moiety is through the alkyl.

"Alkylheteroaryl" means an alkyl-heteroaryl group in which the alkyl and heteroaryl groups are as previously described. The bond to the parent moiety is through the heteroaryl.

"Alkylheterocycloalkyl" means an alkyl-heterocycloalkyl group in which the alkyl and heterocycloalkyl groups are as previously described. The bond to the parent moiety is through the heterocycloalkyl group.

"Alkoxyalkyloxyalkyl" means an alkoxy-alkyl-O-alkyl group in which the alkoxy and alkyl groups are as previously described. The bond to the parent moiety is through the alkyl group.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Haloalkyl" means a halo-alkyl-group in which the alkyl group is as previously described. The bond to the parent moiety is through the alkyl. Non-limiting examples of suitable haloalkyl groups include fluoromethyl and difluoromethyl.

"Heteroaralkyl" or "heteroarylalkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Heteroarylalkenyl" means a heteroaryl-alkenyl group in which the heteroaryl and alkenyl are as previously described. Preferred heteroarylalkenyl contain a lower alkenyl group. The bond to the parent moiety is through the alkenyl group.

"Heterocyclylalkyl" or "heterocycloalkylalkyl" means a heterocyclyl-alkyl group in which the heterocyclyl and alkyl groups are as previously described. The bond to the parent moiety is through the alkyl group.

"Heterocycloalkyloxy" means a heterocycloalkyl-O— group in which the heterocycloalkyl group is as previously described. The bond to the parent moiety is through the ether atom.

"Heteroarylalkoxyalkyl" means a heteroaryl-alkoxyalkyl group in which the heteroaryl and alkoxyalkyl groups are as described above. The bond to the parent moiety is through the alkyl group.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aminoalkyl" means an amino-alkyl group in which the alkyl group is as previously described. The bond to the parent moiety is through the alkyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkenyloxy" means an alkenyl-O— group in which the alkenyl group is as previously described. The bond to the parent moiety is through the ether oxygen.

"Alkynyloxy" means an alkynyl-O— group in which the alkenyl group is as previously described. The bond to the parent moiety is through the ether oxygen.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aralkoxy" or "arylalkoxy" means an aralkyl-O— group in which the aralkyl group is as previously described. The bond to the parent moiety is through the oxygen atom.

"Alkoxyalkyl" or "alkyloxyalkyl" means an alkyl-O-alkyl group in which the alkyl and alkyl groups are as previously described. Non-limiting examples of suitable alkyloxyalkyl groups include methoxymethyl and ethoxymethyl. The bond to the parent moiety is through the alkyl group.

"Aryloxy" means an aryl-O— group in which the aryl group is as previously described. Non-limiting examples of suitable aryloxy groups include phenoxy and naphthoxy. The bond to the parent moiety is through the ether oxygen.

"Aryloxyalkyl" means an aryl-O-alkyl group in which the aryl and alkyl groups are as previously described. Non-limiting examples of suitable aryloxyalkyl groups include phenoxymethyl and naphthoxymethyl. The bond to the parent moiety is through the alkyl group.

"Arylalkoxyalkyl" means an aryl-alkoxyalkyl group in which the aryl and alkoxyalkyl groups are as previously described. The bond to the parent moiety is through the alkyl group.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Arylalkenyl" means an aryl-alkenyl-group in which the aryl and alkenyl groups are as previously described. The bond to the parent moiety is through the alkenyl.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S(O$_2$)— group. Preferred groups are those in which the alkyl group is lower alkyl. The bond to the parent moiety is through the sulfonyl.

"Arylsulfonyl" means an aryl-S(O$_2$)— group. The bond to the parent moiety is through the sulfonyl.

"Cycloalkenyloxy" means a cycloalkenyl-O— group in which the cycloalkenyl group is as previously described. The bond to the parent moiety is through the ether atom.

"Cycloalkylyalkyl" means a cycloalkyl-alkyl group in which the cycloalkyl and alkyl groups are as previously described. The bond to the parent moiety is through the alkyl group.

"Cycloalkyloxy" or "cycloalkoxy" means a cycloalkyl-O— group in which the cycloalkyl group is as previously described. The bond to the parent moiety is through the ether atom.

"Cycloalkyloxyalkyl" means a cycloalkyl-O-alkyl group in which the cycloalkyl and alkyl groups are as previously described. The bond to the parent moiety is through the alkyl group.

"Haloalkoxyalkyl" means a halo alkoxyalkyl group in which the alkoxyalkyl group is as previously described. The bond to the parent moiety is through the alkyl group.

"Heterocyclylalkoxyalkyl" means a heterocyclyl-alkoxyalkyl group in which the alkoxyalkyl group is as previously described. The bond to the parent moiety is through the alkyl group.

The optional double bond represented by ----- means that at least a single bond must be present, but that a double bond can be present; when the double bond is present, $R^{10}$ is absent.

When $R^4$ and $R^5$ join to form a ring with the nitrogen to which they are attached, the rings formed are 1-pyrrolidinyl, 1-piperidinyl and 1-piperazinyl, wherein the piperazinyl ring may also be substituted at the 4-position nitrogen by a group $R^7$.

The above statements, wherein, for example, $R^4$ and $R^5$ are said to be independently selected from a group of substituents, means that $R^4$ and $R^5$ are independently selected when attached to the same nitrogen, but also that where an $R^4$ or $R^5$ variable occurs more than once in a molecule, those occurrences are independently selected. Similarly, each occurrence of $R^{13}$ or $R^{14}$ is independent of any other $R^{13}$ or $R^{14}$ in the same Q ring. Those skilled in the art will recognize that the size and nature of the substituent(s) will affect the number of substituents which can be present.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

The structure ----- in the compound of formula I, represents an optional double bond, the dotted line is a bond or no bond, resulting in a double bond or a single bond, as permitted by the valency requirement; with the proviso that $R^3$ is absent when the carbon to which $R^3$ would be attached is part of a double bond.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs, solvates and co-crystals of the compounds of the invention are also contemplated herein. The term "prodrug", as employed herein, denotes a compound that is a drug precursor which, upon administration to a subject, undergoes chemical conversion by metabolic or chemical processes to yield a compound of Formula I or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

A co-crystal is a crystalline superstructure formed by combining an active pharmaceutical intermediate with an inert molecule that produces crystallinity to the combined form. Co-crystals are often made between a dicarboxlyic acid such as fumaric acid, succinic acid etc. and a basic amine such as the one represented by compound I of this invention in different proportions depending on the nature of the co-crystal. (Rmenar, J. F. et. al. *J. Am. Chem. Soc.* 2003, 125, 8456).

"Effective amount" or "therapeutically effective amount" is meant to describe an amount of compound or a composition of the present invention effective as thrombin receptor antagonists and thus producing the desired therapeutic, ameliorative, inhibitory or preventative effect.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al., Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of Formula I, and salts, solvates, co-crystals and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates, co-crystals and prodrugs of the compounds as well as the salts and solvates, co-crystals of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

Polymorphic forms of the compounds of Formula I, and of the salts, solvates, co-crystals and prodrugs of the compounds of Formula I, are intended to be included in the present invention.

The compounds according to the invention have pharmacological properties; in particular, the compounds of Formula I can be nor-seco himbacine derivatives useful as thrombin receptor antagonists.

Compounds of the invention have at least one asymmetrical carbon atom and therefore all isomers, including enantiomers, stereoisomers, rotamers, tautomers and racemates of the compounds of Formula (I) (where they exist) are contemplated as being part of this invention. The invention includes d and l isomers in both pure form and in admixture, including racemic mixtures. Isomers can be prepared using conventional techniques, either by reacting optically pure or optically enriched starting materials or by separating isomers of a compound of Formula I. Isomers may also include geometric isomers, e.g., when a double bond is present. Polymorphous forms of the compounds of Formula (I), whether crystalline or amorphous, also are contemplated as being part of this invention.

Those skilled in the art will appreciate that for some of the compounds of Formula I, one isomer will show greater pharmacological activity than other isomers.

A typical preferred compound of the present invention has the following stereochemistry:

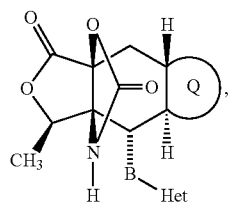

with compounds having that absolute stereochemistry being more preferred.

Those skilled in the art will appreciate that for some compounds of Formula I, one isomer will show greater pharmacological activity than other isomers.

Compounds of the invention are prepared by a two-step procedure in which the ring formed by —$(R^3)_{n7}$—X—Y—N($R^8$)— is synthesized from an alcohol intermediate. The process for preparing compounds wherein Y is —C(O)— is described by Espino et al in *Angew. Chem. Int. Ed.*, 40, 3 (2001), p. 598-600, and the process for preparing compounds wherein Y is —$SO_2$— is described by Espino et al in *J. Am. Chem. Soc.*, 123 (2001), p. 6935-6936.

The alcohol intermediates can be obtained by the methods disclosed in any of U.S. Pat. No. 6,063,847, U.S. Pat. No. 6,326,380, U.S. Pat. No. 6,645,987 and U.S. Ser. No. 10/271,715, all of which are incorporated herein by reference.

Following are examples of preparing starting materials and compounds of formula I. In the procedures, the following abbreviations are used:

| | |
|---|---|
| rt | room temperature |
| Ac | acetyl |
| Me | methyl |
| Et | ethyl |
| Ph | phenyl |
| TLC | thin layer chromatography |

Example 1

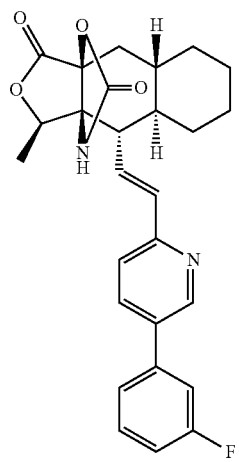

Step 1:

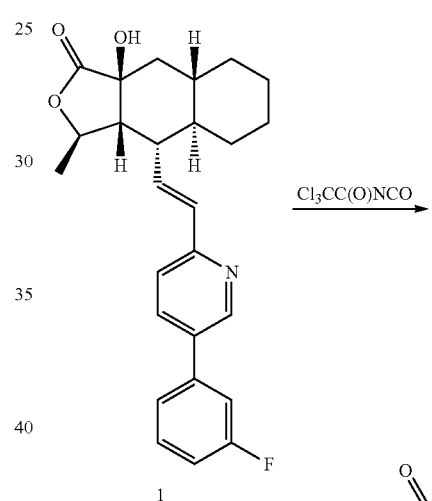

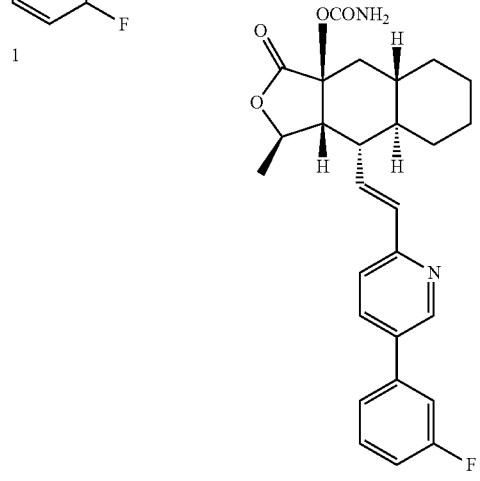

Compound 1 (0.32 g, 0.76 mmol, prepared as described in U.S. Pat. No. 6,063,847; see example 4D) was stirred with trichloro-acetyl isocyanate (0.12 ml, 1.5 eq.) in $CH_2Cl_2$ (10 ml) at rt for 15 min. The mixture was concentrated in vacuo. The residual solid was dissolved in MeOH (10 ml) and treated with $K_2CO_3$ (10 mg). The mixture was stirred at rt for 45 min, diluted with $CH_2Cl_2$ (75 ml), and washed with $NH_4Cl$ (sat.). The organic layer was dried ($MgSO_4$) and concentrated in vacuo. Flash chromatography of the residue on a silica gel column with $EtOAc$-$CH_2Cl_2$ (15-85) as eluent gave compound 2 (0.25 g, 71%). MS (ESI) m/z 465.1 (MH$^+$).

Step 2:

Compound 2 (0.11 g, 0.24 mmol) was refluxed with MgO (48 mg, 5 eq.), PhI(OAc)$_2$ (185 mg, 3 eq.), and Rh$_2$(OAc)$_4$ (20 mg, 0.2 eq.) in $CH_2Cl_2$ (10 ml) for 20 h. The mixture was filtered and the filtrate was concentrated in vacuo. Preparative TLC separation of the residue with concentrated aqueous ammonia-EtOAc—$CH_2Cl_2$(0.1-15-85) as eluent gave the title compound (50 m g). MS (ESI) m/z 463.1 (MH$^+$).

Example 2

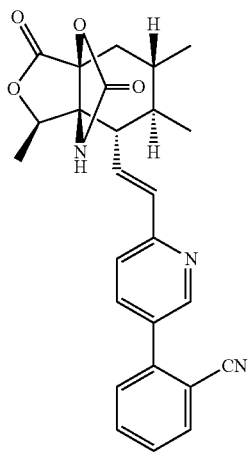

The title compound was prepared using a procedure analogous to Example 1, but starting with the alcohol of Example 8CLA in U.S. Pat. No. 6,645,987. MS (LCMS) m/z 444 (MH$^+$).

Using the procedure of Example 2, the following compounds were also prepared from the appropriate starting materials:

Example 3

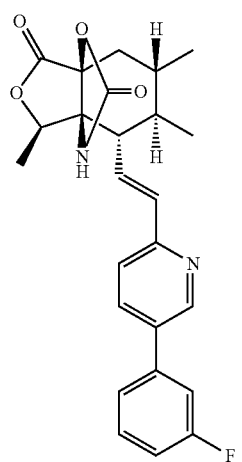

MS (LCMS) m/z 437 (MH$^+$)

Example 4

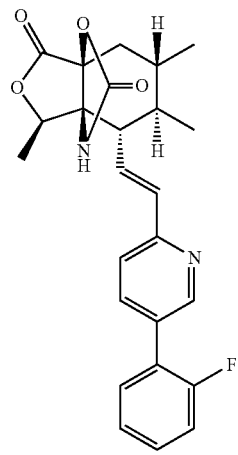

MS (LCMS) m/z 437 (MH$^+$)

Example 5

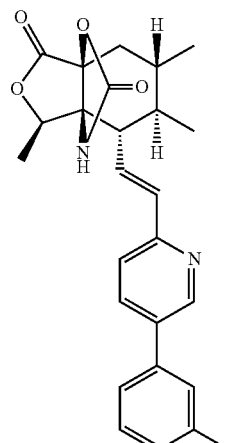

MS (LCMS) m/z 444 (MH$^+$).

Further embodiments of the invention encompass the administration of compounds of Formula I along with at least one additional agent. The contemplated additional agent is one that differs in either atomic make up or arrangement from the compounds of Formula I. Additional agents that can be used in combination with the novel compounds of this invention include drugs that are useful in treating thrombosis-related diseases including thrombosis, atherosclerosis, restenosis, hypertension, angina pectoris, angiogenesis related disorders, arrhythmia, a cardiovascular or circulatory disease or condition, heart failure, myocardial infarction, glomerulonephritis, thrombotic stroke, thromboembolytic stroke, peripheral vascular diseases, cerebral ischemia, rheumatoid arthritis, rheumatism, astrogliosis, a fibrotic disorder of the liver, kidney, lung or intestinal tract, systemic lupus erythematosus, multiple sclerosis, osteoporosis, glomerulonephritis, renal disease, acute renal failure, chronic renal failure, renal vascular homeostasis, renal ischemia, bladder inflammation, diabetes, diabetic neuropathy, cerebral stroke, cerebral ischemia, nephritis, cancer, melanoma, renal cell carcinoma, neuropathy and/or malignant tumors, neurodegenerative and/or neurotoxic diseases, conditions, or injuries, inflammation, asthma, glaucoma, macular degeneration, psoriasis, endothelial dysfunction disorders of the liver, kidney or lung inflammatory disorders of the lungs and gastrointestinal tract, respiratory tract disease or condition, radiation fibrosis, endothelial dysfunction, periodontal diseases or wounds or a spinal cord injury, or a symptom or result thereof, as well as other disorders in which thrombin and its receptor play a pathological role.

Suitable cardiovascular agents are selected from the group consisting of thromboxane A2 biosynthesis inhibitors; thromboxane antagonists; adenosine diphosphate inhibitors; cyclooxygenase inhibitors; angiotensin antagonists; endothelin antagonists; phosphodiesterase inhibitors; angiotensin converting enzyme inhibitors; neutral endopeptidase inhibitors; anticoagulants; diuretics; platelet aggregation inhibitors; and GP IIb/IIIa antagonists.

Preferred types of drugs for use in combination with the novel compounds of this invention are thromboxane A2 biosynthesis inhibitors, GP IIb/IIIa antagonists, thromboxane antagonists, adenosine diphosphate inhibitors, cyclooxygenase inhibitors, angiotensin antagonists, endothelin antagonists, angiotensin converting enzyme inhibitors, neutral endopeptidase inhibitors, anticoagulants, diuretics, and platelet aggregation inhibitors.

In particular, suitable cardiovascular agents are selected from the group consisting of aspirin, seratrodast, picotamide and ramatroban, clopidogrel, meloxicam, rofecoxib, celecoxib, valsartan, telmisartan, candesartran, irbesartran, losartan, eprosartan, tezosentan, milrinoone, enoximone, captopril, enalapril, enaliprilat, spirapril, quinapril, perindopril, ramipril, fosinopril, trandolapril, lisinopril, moexipril, benazepril, candoxatril, ecadotril, ximelagatran, fondaparin, enoxaparin, chlorothiazide, hydrochlorothiazide, ethacrynic acid, furosemide, amiloride, abciximab, eptifibatide, parsugrel and fragmin.

Especially preferred for use in the combinations are aspirin, cangrelor, clopidogrel bisulfate, parsugrel and fragmin.

When the invention comprises a combination of a compound of Formula I and another agent, the two active components may be co-administered simultaneously or sequentially, or a single pharmaceutical composition comprising a compound of Formula I and another agent in a pharmaceutically acceptable carrier can be administered. The components of the combination can be administered individually or together in any conventional dosage form such as capsule, tablet, powder, cachet, suspension, solution, suppository, nasal spray, etc. The dosage of the additional agent can be determined from published material, and may range from 1 to 1000 mg per dose.

In this specification, the term "at least one compound of Formula I" means that one to three different compounds of Formula I may be used in a pharmaceutical composition or method of treatment. Preferably one compound of Formula I is used. Similarly, the term "one or more additional cardiovascular agents" means that one to three additional drugs may be administered in combination with a compound of Formula I; preferably, one additional compound is administered in combination with a compound of Formula I. The additional agents can be administered sequentially or simultaneously with reference to the compound of Formula I.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *The Science and Practice of Pharmacy*, 20$^{th}$ Edition, (2000), Lippincott Williams & Wilkins, Baltimore, Md.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 150 mg, preferably from about 1 mg to about 75 mg, more preferably from about 1 mg to about 50 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 75 mg/day, in two to four divided doses.

When separate compounds of Formula I and the other agents are to be administered as separate compositions, they can be provided in a kit comprising in a single package, one container comprising a compound of Formula I in a pharmaceutically acceptable carrier, and a separate container comprising another cardiovascular agent in a pharmaceutically acceptable carrier, with the compound of Formula I and the other agent being present in amounts such that the combination is therapeutically effective. A kit is advantageous for administering a combination when, for example, the components must be administered at different time intervals or when they are in different dosage forms.

The activity of the compounds of formula I can be determined by the following procedures.

In Vitro Testing Procedure for Thrombin Receptor Antagonists:

Preparation of [$^3$H]haTRAP

A(pF-F)R(ChA)(hR)(I$_2$—Y)—NH$_2$ (1.03 mg) and 10% Pd/C (5.07 mg) were suspended in DMF (250 µl) and diisopropylethylamine (10 µl). The vessel was attached to the tritium line, frozen in liquid nitrogen and evacuated. Tritium gas (342 mCi) was then added to the flask, which was stirred at room temperature for 2 hours. At the completion of the reaction, the excess tritium was removed and the reacted peptide solution was diluted with DMF (0.5 ml) and filtered to remove the catalyst. The collected DMF solution of the crude peptide was diluted with water and freeze dried to remove the labile tritium. The solid peptide was redissolved in water and the freeze drying process repeated. The tritiated peptide ([$^3$H] haTRAP) was dissolved in 0.5 ml of 0.1% aqueous TFA and purified by HPLC using the following conditions: column, Vydac™ C18, 25 cm×9.4 mm I.D.; mobile phase, (A) 0.1% TFA in water, (B) 0.1% TFA in CH$_3$CN; gradient, (A/B) from 100/0 to 40/60 over 30 min; flow rate, 5 ml/min; detection, UV at 215 nm. The radiochemical purity of [$^3$H]haTRAP was 99% as analyzed by HPLC. A batch of 14.9 mCi at a specific activity of 18.4 Ci/mmol was obtained.

Preparation of Platelet Membranes

Platelet membranes were prepared using a modification of the method of Natarajan et al. (Natarajan et al, *Int. J. Peptide Protein Res.* 45:145-151 (1995)) from 20 units of platelet concentrates obtained from the North Jersey Blood Center (East Orange, N.J.) within 48 hours of collection. All steps were carried out at 4° C. under approved biohazard safety conditions. Platelets were centrifuged at 100×g for 20 minutes at 4° C. to remove red cells. The supernatants were decanted and centrifuged at 3000×g for 15 minutes to pellet platelets. Platelets were re-suspended in 10 mM Tris-HCl, pH 7.5, 150 mM NaCl, 5 mM EDTA, to a total volume of 200 ml and centrifuged at 4400×g for 10 minutes. This step was repeated two additional times. Platelets were re-suspended in 5 mM Tris-HCl, pH 7.5, 5 mM EDTA to a final volume of approximately 30 ml and were homogenized with 20 strokes in a Dounce™ homogenizer. Membranes were pelleted at 41,000×g, re-suspended in 40-50 ml 20 mM Tris-HCl, pH 7.5, 1 mM EDTA, 0.1 mM dithiothreitol, and 10 ml aliquots were frozen in liquid N$_2$ and stored at −80° C. To complete membrane preparation, aliquots were thawed, pooled, and homogenized with 5 strokes of a Dounce homogenizer. Membranes were pelleted and washed 3 times in 10 mM triethanolamine-HCl, pH 7.4, 5 mM EDTA, and re-suspended in 20-25 ml 50 mM Tris-HCl, pH 7.5, 10 mM MgCl$_2$, 1 mM EGTA, and 1% DMSO. Aliquots of membranes were frozen in liquid N$_2$ and stored at −80° C. Membranes were stable for at least 3 months. 20 units of platelet concentrates typically yielded 250 mg of membrane protein. Protein concentration was determined by a Lowry assay (Lowry et al., *J. Biol. Chem.*, 193:265-275 (1951)).

High Throughput Thrombin Receptor Radioligand Binding Assay

Thrombin receptor antagonists were screened using a modification of the thrombin receptor radioligand binding assay of Ahn et al. (Ahn et al., *Mol. Pharmacol.*, 51:350-356 (1997)). The assay was performed in 96 well Nunc plates (Cat. No. 269620) at a final assay volume of 200 µl. Platelet membranes and [$^3$H]haTRAP were diluted to 0.4 mg/ml and 22.2 nM, respectively, in binding buffer (50 mM Tris-HCl, pH 7.5, 10 mM MgCl$_2$, 1 mM EGTA, 0.1% BSA). Stock solutions (10 mM in 100% DMSO) of test compounds were further diluted in 100% DMSO. Unless otherwise indicated, 10 µl of diluted compound solutions and 90 µl of radioligand (a final concentration of 10 nM in 5% DMSO) were added to each well, and the reaction was started by the addition of 100 µl of membranes (40 µg protein/well). The binding was not significantly inhibited by 5% DMSO. Compounds were tested at three concentrations (0.1, 1 and 10 µM). The plates were covered and vortex-mixed gently on a Lab-Line™ Titer Plate Shaker for 1 hour at room temperature. Packard UniFilter™ GF/C filter plates were soaked for at least 1 hour in 0.1% polyethyleneimine. The incubated membranes were harvested using a Packard FilterMate™ Universal Harvester and were rapidly washed four times with 300 µl ice cold 50 mM Tris-HCl, pH 7.5, 10 mM MgCl$_2$, 1 mM EGTA. MicroScint™ 20 scintillation cocktail (25 µl) was added to each well, and the plates were counted in a Packard TopCount™ Microplate Scintillation Counter. The specific binding was defined as the total binding minus the nonspecific binding observed in the presence of excess (50 µM) unlabeled haTRAP. The % inhibition by a compound of [$^3$H]haTRAP binding to thrombin receptors was calculated from the following relationship:

$$\% \text{ Inhibition} = \frac{\text{Total binding} - \text{Binding in the presence of a test compound}}{\text{Total binding} - \text{Nonspecific binding}} \times 100$$

Materials

A(pF-F)R(ChA)(hR)Y—NH$_2$ and A(pF-F)R(ChA)(hR)(I$_2$—Y)—NH$_2$, were custom synthesized by AnaSpec Inc. (San Jose, Calif.). The purity of these peptides was >95%. Tritium gas (97%) was purchased from EG&G Mound, Miamisburg, Ohio. The gas was subsequently loaded and stored on an IN/US Systems Inc. Trisorber. MicroScint™ 20 scintillation cocktail was obtained from Packard Instrument Co.

Cannabinoid CB$_2$ Receptor Binding Assay

Binding to the human cannabinoid CB$_2$ receptor was carried out using the procedure of Showalter, et al. (1996, *J. Pharmacol Exp Ther.* 278(3), 989-99), with minor modifications. All assays were carried out in a final volume of 100 ul. Test compounds were re-suspended to 10 mM in DMSO, then serially diluted in 50 mM Tris, pH 7.1, 3 mM MgCl$_2$, 1 mM EDTA, 50% DMSO. Aliquots (10 ul) of each diluted sample were then transferred into individual wells of a 96-well microtiter plate. Membranes from human CB$_2$ transfected CHO/Ki cells (Receptor Biology, Inc) were re-suspended in binding buffer (50 mM Tris, pH 7.1, 3 mM MgCl2, 1 mM EDTA, 0A % fatty acid free bovine serum albumin), then added to the binding reaction (~15 ug in 50 ul per assay). The reactions were initiated with the addition of [$^3$H] CP-55, 940 diluted in binding buffer (specific activity=180 Ci/mmol; New England Nuclear, Boston, Mass.). The final ligand concentration in the binding reaction was 0.48 nM. Following incubation at room temperature for 2 hours, membranes were harvested by filtration through pretreated (0.5% polyethylenimine; Sigma P-3143) GF-C filter plates (Unifilter-96, Packard) using a TomTec™ Mach 3U 96-well cell harvester (Hamden, Conn.). Plates were washed 10 times in 100 ul binding buffer, and the membranes allowed to air dry. Radioactivity on membranes was quantitated following addition of Packard Omniscint™ 20 scintillation fluid using a TopCount™ NXT Microplate Scintillation and Luminescence Counter (Packard, Meriden, Conn.). Non-linear regression analysis was performed using Prism™ 20b. (GraphPad Software, San Diego, Calif.).

Using the test procedures described above, representative compounds of formula I were found to have thrombin receptor $IC_{50}$ values (i.e., the concentration at which a 50% inhibition of thrombin receptor was observed) of 1 to 1000 nM, preferably 1-100 nM, more preferably 1-50 nM.

We claim:

1. A compound represented by structural formula:

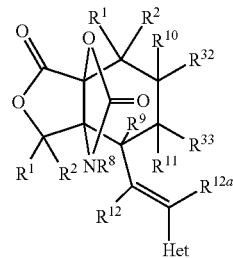

or a pharmaceutically acceptable salt of said compound, wherein

Het is a pyridyl group which is substituted by 1 to 4 moieties, W, wherein each W is independently selected from the group consisting of hydrogen, alkyl or $R^{21}$-substituted-aryl;

$R^1$ and $R^2$ are independently selected from the group consisting of hydrogen, alkyl, fluoroalkyl, difluoroalkyl, trifluoroalkyl, hydroxyl, hydroxyalkyl or alkoxy;

$R^8$ is H or alkyl;

$R^9$ is H;

$R^{10}$ and $R^{11}$ are independently selected from the group consisting of H or alkyl;

$R^{12}$ and $R^{12a}$ are independently selected from the group consisting of hydrogen, alkyl and halogen;

$R^{17}$ is H or alkyl; and $R^{21}$ is 1 to 3 moieties and each $R^{21}$ is independently selected from the group consisting of hydrogen, —CN, —CF$_3$, —OCF$_3$, halogen, —NO$_2$, alkyl, —OH, alkoxy, alkylamino-, di-(alkyl)amino- or —C(O)(OR$^{17}$)—;

$R^{32}$ is hydrogen or alkyl; and $R^{33}$ is hydrogen or alkyl.

2. The compound of claim 1 wherein R1 and R2 located on the cyclohexane ring are H.

3. The compound of claim 2 wherein on the furanone ring $R^1$ is H and $R^2$ is alkyl.

4. The compound of claim 1 wherein $R^8$ is H.

5. The compound of claim 2 wherein $R^{32}$ is alkyl, $R^{33}$ is alkyl, $R^{10}$ is H, and $R^{11}$ is H.

6. The compound of claim 2 wherein $R^{32}$ and $R^{33}$ are each methyl.

7. The compound of claim 1 wherein $R^{32}$ is alkyl, $R^{33}$ is alkyl, $R^{10}$ is H, and $R^{11}$ is H.

8. The compound of claim 1 wherein $R^9$ is H.

9. A compound having the formula

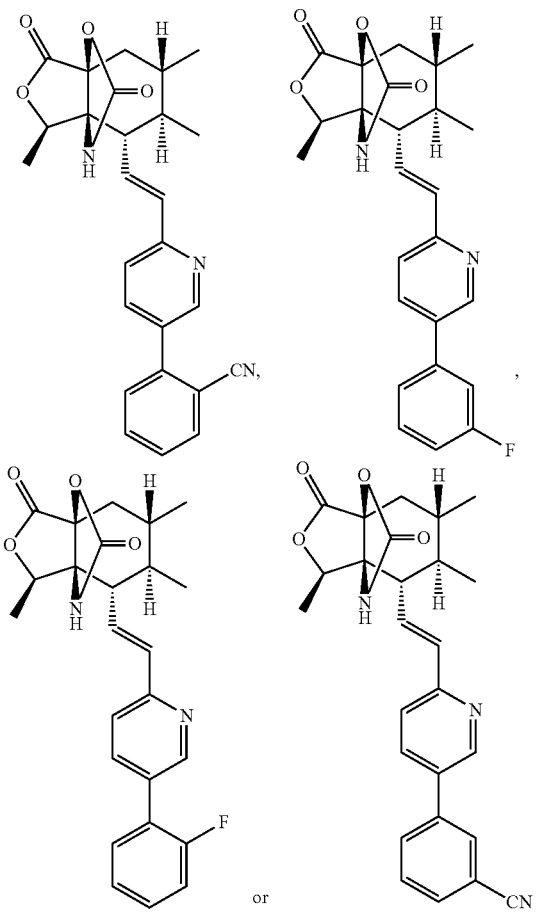

or a pharmaceutically acceptable salt thereof.

10. A compound which has the formula:

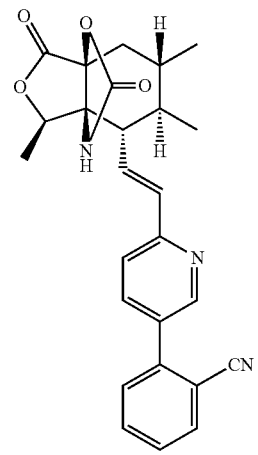

or a pharmaceutically acceptable salt thereof.

11. A pharmaceutical composition comprising an effective amount of a compound of claim 1 and a pharmaceutically acceptable carrier.

* * * * *